United States Patent [19]

Lang et al.

[11] 4,293,542
[45] Oct. 6, 1981

[54] COSMETIC COMPOSITION FOR IMPARTING TO HUMAN SKIN A COLORATION RESEMBLING A NATURAL TAN

[75] Inventors: Gérard Lang, Epinay-sur-Seine; Serge Forestier, Claye-Souilly, both of France

[73] Assignee: L'Oreal, Paris, France

[21] Appl. No.: 793,316

[22] Filed: May 3, 1977

[30] Foreign Application Priority Data

May 3, 1976 [FR] France .............................. 76 13164

[51] Int. Cl.³ ...................... A61K 7/00; A61K 7/021; A61K 7/44; A61K 31/44
[52] U.S. Cl. ........................................ 424/47; 424/60; 424/63; 424/263
[58] Field of Search ...................... 424/47, 60, 63, 263

[56] References Cited

U.S. PATENT DOCUMENTS

| | | | |
|---|---|---|---|
| 2,974,089 | 3/1961 | Alexander et al. | 424/60 |
| 3,113,072 | 12/1963 | Goodhue et al. | 424/263 |
| 3,150,041 | 9/1964 | Goodhue et al. | 424/263 X |
| 3,193,455 | 7/1965 | Reinert | 424/263 |

FOREIGN PATENT DOCUMENTS 1288282 2/1962 France .
3691M 11/1965 France .
2147121 3/1973 France .
1355461 6/1974 United Kingdom .

*Primary Examiner*—Allen J. Robinson
*Attorney, Agent, or Firm*—Cushman, Darby & Cushman

[57] ABSTRACT

A cosmetic composition for imparting to human skin after exposure to sunlight a coloration resembling a natural tan comprising a cosmetic vehicle suitable for topical application to the skin and an effective amount of at least one compound of the formula

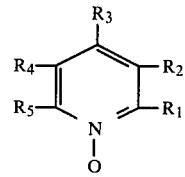

wherein $R_1$ represents hydrogen or amino; $R_2$ represents hydrogen, lower alkyl or amino; $R_3$ represents hydrogen, lower alkyl or amino; $R_4$ represents hydrogen, lower alkyl or chlorine; and $R_5$ represents hydrogen, lower alkyl or hydroxy, or amino when $R_1$ is amino, with the proviso that $R_1$, $R_2$ and $R_3$ are not simultaneously amino; and at least one of $R_1$, $R_2$, $R_3$ means amino or an acid addition salt thereof.

35 Claims, No Drawings

COSMETIC COMPOSITION FOR IMPARTING TO HUMAN SKIN A COLORATION RESEMBLING A NATURAL TAN

The present invention relates to a new cosmetic composition for imparting to human skin a coloration essentially comparable to a natural tan.

As is known, natural tanning of human skin is due to melanization resulting from exposure of the skin to light rays having a wave length between 280 and 400 millimicrons. However, this exposure which is necessary to obtain a tan appearance of the skin very often, and especially when the exposure is for a long period of time, can cause not only very painful burns but also for those with sensitive skin, long term skin problems, and for many very unesthetic peeling of the skin.

To avoid these disadvantages, it is possible to apply to the skin compositions containing a more or less selective solar filter. However, if these compositions are successful in avoiding solar burns, they generally also retard by reason of their very nature, the production of the desired tan appearance. This often prompts persons who desire a rapid tanning not to use these compositions thereby risking encountering the above mentioned disadvantages.

Heretofore, it has also been proposed to use compositions for imparting to the skin an artificial tan appearance. A particular composition of this type is one which is based on dihydroxy acetone, disclosed for instance in French Pat. No. 1,250,185. The tan obtained through the use of dihydroxy acetone results from a reaction between the active product and the protein components of the skin, independently of an exposure to the sun.

The use of such compositions, however, has several drawbacks in achieving an artificial tan which resembles as much as possible a natural tan.

In effect, because of the mechanism at the outset, very often after successive applications different shades result depending on the amount of callous skin treated. Further, the coloration obtained is irregularly removed by washing which also leads to undesired shade variations.

Moreover the production of a skin coloration which is independent of exposure to sunlight accentuates for many the artificiality of the tan. Thus, even though many people may deisre to get tanned rapidly, nonetheless they generally desire that the tanning be effected as naturally as possible, that is to say, by exposure to the sun.

It has now been found that by applying to the skin a composition containing at least one pyridine derivative a coloration essentially similar to a natural tan can be achieved in less time than is required to obtain a natural tan after exposure of the thus treated skin to ultra-violet rays having a wave length between 320 and 400 millimicrons.

It has also been found that this coloration does not result from a reaction of the active product with the protein components of the skin. The tan coloration achieved is uniform; it covers completely the areas of the skin exposed to the sun rays and it is removed in a regular manner with washing.

The compounds employed in the composition of the present invention also do not react with solar filters conventionally employed in this type of composition. Therefore, these compounds can be used in combination with these known solar filters, thus providing not only protection for the skin but also a rapid tanning of the skin.

It is therefore a principal object of the present invention to provide a cosmetic composition for imparting to human skin a coloration essentially identical to a natural tan, after exposure of the skin to radiation having a wave length between 320 and 400 millimicrons, said composition containing at least one pyridine derivative.

Another object of the present invention is the provision of a process for coloring the skin by the action of ultra violet rays.

The composition according to the present invention comprises a cosmetic vehicle for topical application to the skin and an effective amount of at least one pyridine derivative having the formula:

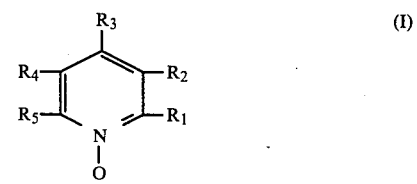

wherein:

$R_1$ represents hydrogen or amino;

$R_2$ represents hydrogen, lower alkyl having preferably from 1–4 carbon atoms or amino;

$R_3$ represents hydrogen, lower alkyl having preferably from 1–4 carbon atoms or amino;

$R_4$ represents hydrogen, lower alkyl having preferably from 1–4 carbon atoms or chlorine;

$R_5$ represents hydrogen, lower alkyl having preferably from 1–4 carbon atoms or hydroxyl, or when $R_1$ is amino, $R_5$ can also represent amino; with the proviso that $R_1$, $R_2$ and $R_3$ are not simultaneously an amino group and at least one of $R_1$, $R_2$ and $R_3$ is amino.

In a preferred embodiment of the invention, the lower alkyl is methyl.

Representative pyridine derivatives usefully employed in the present invention include:

2-amino pyridine N-oxide,
2-amino-3-methyl pyridine N-oxide,
2-amino-4-methyl pyridine N-oxide,
2-amino-5-methyl pyridine N-oxide,
2-amino-6-methyl pyridine N-oxide,
2-amino-4,6-dimethyl pyridine N-oxide,
2-amino-5-chloro pyridine N-oxide
2,6-diamino pyridine N-oxide,
3-amino pyridine N-oxide,
3-amino-6-methyl pyridine N-oxide,
3-amino-6-hydroxy pyridine N-oxide and
4-amino pyridine N-oxide.

The salts of addition with mineral or organic acids of the said pyridine derivative can also be employed. Preferably the addition salts are the hydrochloride, the sulfate, the acetate, the lactate, the perchlorate, the citrate and the stearate thereof.

The composition in accordance with the present invention can contain one or more pyridine derivatives defined above which is present in an amount between 0.5 and 10, and preferably between 1 and 5, percent by weight relative to the total weight of the composition.

The amount of the pyridine derivative can vary depending on the nature of the derivative itself as well as the coloration desired; the more pronounced the color desired, generally a greater amount of pyridine derivative is used. The pH of the composition of the present invention is generally between 3 and 8.5 and preferably between 4 and 6.

The cosmetic composition of this invention should be provided in a form which can be uniformly spread on the skin so as to obtain even distribution of the pyridine derivative thereon. Thus, the composition can be provided in the form of a lotion, a gel or an emulsion, the preferred form being an emulsion having a continuous aqueous phase.

The composition can also be provided in the form of an aqueous solution, preferably a hydroalcoholic solution or a glycerin-alcoholic solution or even a glycerine hydroalcoholic solution. In these alcohol containing solutions, the alcohol is preferably ethanol or isopropanol and it is present in an amount between 10 and 90 weight percent, preferably between 40 and 60 weight percent relative to the total weight of the composition. The glycerine, when present, is employed, preferably in an amount between 0.5 and 5 weight percent, more preferably in an amount of 2 weight percent based on the total weight of the composition. This cosmetic composition can also contain a wetting agent including oxyethylenated derivatives such as lanolin ethoxylated with 25 moles of ethylene oxide or polyethylene glycol.

The composition, in lotion form, can also be an oleoalcohol composition containing preferably a vegetable oil such as, for example, colza oil, olive oil, peanut oil, coconut oil and palm oil; a lower alkyl ester such as isopropyl myristate or isopropyl palmitate; and a lower alcohol having preferably 1–4 carbon atoms and more particularly ethanol. The vegetable oil is present preferably in an amount of 0.2 to 5 weight percent; the alkyl ester, in an amount of 5 to 40 weight percent; and the alcohol, in an amount of 35–80, preferably 40 to 75 weight percent, based on the total weight of the composition. The concentration of the pyridine derivative of formula I is preferably between 0.5 and 3 weight percent due to its reduced solubility in this oleo-alcohol carrier or vehicle.

The composition of the present invention can also be packaged under pressure in an aerosol container together with a gaseous propellant selected from nitrogen, nitrous oxide, a volatile hydrocarbon such as butane, isobutane or propane or, preferably, a fluorinated hydrocarbon sold under the name of Freon and in particular such fluorocarbons as dichlorodifluoromethane (Freon 12), dichlorotetrafluoromethane (Freon 114) and trichloromonofluoromethane (Freon 11). These propellants can be used singly or in combination.

When the composition of this invention is in the form of an aqueous gel it includes, generally, a surfactant selected from a fatty alcohol having 12–18 carbon atoms and oxyethylenated with 4–15 and preferably with 6–12 moles of ethylene oxide; nonylphenol oxyethylenated with 6–12 moles of ethylene oxide; a carboxylic derivative of imidazole; and a gel forming agent selected from a cellulose ether, carboxy methyl cellulose or a crosslinked polyacrylic acid sold under the tradename Carbopol.

The aqueous gel can also include a silicone oil, which when it is present is emulsified by the surfactant.

The surfactant is present preferably in an amount from 1 to 25 and, preferably, from 1 to 10 weight percent; the gel forming agent, in an amount from 0.5 to 5, and preferably from 1 to 2.5 weight percent; and the silicone oil, in an amount up to 2 weight percent and preferably 0.1 weight percent, based on the total weight of the composition.

In a particularly preferred emboiment of the invention, the composition is provided in the form of an oil-in-water emulsion. This emulsion contains a surfactant, an oil, a thickening agent and a humectant. The surfactant which is present, preferably in an amount from 2 to 20, and more preferably, from 10 to 16 weight percent, is selected from such emulsifying agents as a fatty alcohol having 12–18 carbon atoms and oxyethylenated with 10–15 moles of ethylene oxide; isopropyl palmitate; isopropyl myristate; glycerol monostearate; polyoxyethylenated sorbitan monostearate; a self-emulsifying wax selected from partially sulfated or partially oxyethylenated cetyl-stearyl alcohols; and a mixture of these emulsifying agents or waxes. The oil or fatty phase of this emulsion is present in an amount between 10 and 50 weight percent and can be a light petrolatum oil; perhydrosqualene; a vegetable oil such as sweet almond oil, ricin oil, colza oil, olive oil, peanut oil, coconut oil and palm oil; a fatty alcohol having for example 7 carbon atoms and a saturated fatty acid having, for example, 18 carbon atoms. The thickening agent employed in this emulsion is present in an amount between 0 and 6 weight percent and can be, for instance, starch, a crosslinked polyacrylic acid sold under the mark Carbopol or diethylene glycol stearate. The humectant in the emulsion is preferably glycerine and is present in an amount of 0 to 15 weight percent.

When the surfactant employed in this emulsion is a partially sulfated or partially oxyethylenated cetyl-stearyl alcohol, the non-oxyethylenated or non-sulfated portion thereof serves as the oil or fatty phase in this oil-in-water emulsion.

This oil-in-water emulsion can be provided as a milk or a cream, but it can also be packaged under pressure in an aerosol container together with an aerosol propellant such as defined above.

The composition of the present invention can also contain various other components or adjuvants conventionally employed in cosmetic preparations of this type. Representative adjuvants include principally perfumes, preservatives, softening agents, super-fatting agents, emollients, anti-foam agents and the like.

The pH of the composition of the present invention can be adjusted by the addition thereto of an acid such as acetic acid, or citric acid, or a base, such as monoethanolamine or triethanolamine.

The composition according to the present invention can also contain a solar filter so as to protect the skin against harmful radiations. The inclusion of a filter also permits over a period of time to modulate the deepening of the color as a function of the amount of solar filter in the composition, as well as the nature of the said solar filter.

Representative solar filters usefully employed in the present invention include such known materials as the following salicylic acid derivatives: amyl, phenyl, benzyl, methyl, glyceryl, dipropylene glycol and in particular, 2-ethyl hexyl, 3,3,5-trimethyl hexyl, 2-phenyl, sodium, triethanolamine and benzyl methyl eugenol salicylates;

the following cinnamic acid derivatives: methyl and benzyl esters, α-phenyl cinnamo nitrile, butyl cinnamoyl pyruvate; dihydroxy cinnamic acid derivatives such as umbelliferone, methyl umbeliferone, methyl acetoumbelliferone; tri-hydroxy cinnamic acid derivatives such as esculetine, methyl esculetine, daphnetine and esculine and daphine glucosides; the cinnamic acid derivatives more particularly preferred are 2-ethoxy ethyl paramethoxy cinnamate, isobutyl salicyl cinnamate, ethyl para methoxy cinnamate, cyclohexyl paramethoxy cinnamate, ethyl hexyl para-methoxy cinnamate, the esters of substituted cinnamic acid and the potassium salt of methoxy cinnamic acid;

the following para-amino benzoic acid derivatives: ethyl, isobutyl and glyceryl ethers of p-amino benzoic acid, 4-amino benzoic acid polyoxyethylenated with 25 moles of ethylene oxide, the monoglyceryl ester of paraamino benzoic acid, oxyethylenated derivatives of para amino benzoic acid, amyl para dimethyl benzoate, butyl para dimethyl amino benzoate, ethyl para dimethylamino benzoate, methyl para dimethylamino benzoate and ethyl para diethylamino benzoate;

the following benzophenone derivatives: substituted benzophenone sold under the commercial names "UVINUL 410" and "UVINUL 490", 2,4-dihydroxy benzophenone, 2,2'-dihydroxy-4-methoxy benzophenone, 2,2'-dihydroxy-4,4'-dimethoxy benzophenone, 2-hydroxy-4-N-ethyl benzophenone, 2-hydroxy-4-methoxy benzophenone, 2-hydroxy-4-methoxy benzophenone 5-sulphonic acid and its sodium salt, 2-hydroxy-4-methoxy-4'-methyl benzophenone, 2-hydroxy-5-chloro benzophenone 2'-isooctyl carboxylic acid ester, 2,2'-dihydroxy-4,4'-dimethoxy benzophenone 5-sulphonic acid and its sodium salt, and 2,2',4,4'-tetrahydroxy benzophenone;

the following coumarin derivatives: hydroxy coumarin, dihydroxy coumarin and 7-diethylamino-4-methyl coumarin;

the following azoles: benzotriazole derivatives such as 5'-methyl-2'-hydroxy phenyl benzotriazole and 2,2'-dihydroxy-3',5'-ditertio butyl phenyl-5-chloro benzotriazole;

the following imidazole derivatives: imidazole 4-acrylic acid, 2-phenyl benzimidazole-5-sulfonic acid, 2-acetyl-3-bromoindazole, phenyl benzoxazole, methyl naphtoxazole and various arylbenzothiazoles;

the following naphtosulfonates: the sodium salts of 2-naphtol 3,6-disulfonic acid and naphtol 6,8-disulfonic acid;

the following quinine salts: the disulfate, the sulfate, the chloride, the oleate, the tannate; the quinolein derivatives including the salts of 8-hydroxy quinolein or the salts of 2-phenyl quinolein, tannic acid and its derivatives such as the hexaethyl ether thereof;

acetanilide, benzalhydrazine and dibenzalhydrazine;

hydroquinone and its derivatives such as 2,4-dibenzoyl resorcinol, unsaturated cyclic ketone, aromatic esters of higher aliphatic alcohol, sesame oil, sodium 3,4-dimethoxy phenyl glyoxylate, digaloyl trioleate, benzoyl phenyl carbinol, benzylidene camphor and its derivatives, 2-phenyl indol and its derivatives.

Among these solar filters, the last two types are described more fully in French Pat. Nos. 7334140, 7405427, 7428478 and 7526732.

These solar filters are used in an amount between 0.5 and 5 and preferably between 1 and 3 weight percent. relative to the total weight of the composition.

The more particularly preferred solar filters include benzylidene camphor, ethyl hexyl para methoxy cinnamate, amyl para dimethylamino benzoate, benzophenone derivatives such as 5-benzoyl-4-hydroxy-2-methoxy benzene sulfonic acid, hydroxy propylenated derivatives of ethyl p-amino benzoate, and the diethanolamine salt of p-methoxy cinnamic acid.

The cosmetic composition of this invention is stored out of contact with light and is perfectly stable.

The process for coloring the skin in accordance with the present invention comprises applying to the skin the composition defined above using any procedure so as to obtain a uniform distribution of the composition on the skin and exposing the thus treated skin to light rays having a wave length of 320 to 400 millimicrons. After a period of time which is clearly shorter than would be necessary to obtain a natural tan, a skin coloration, essentially comparable to the said natural tan, is obtained. This process also makes it possible to modulate, over a period of time, the appearance of this coloration by the addition to the composition of a solar filter as defined above. The appearance of the coloration if it is delayed by the inclusion of a solar filter nonetheless is effected quite rapidly relative to the exposure time required to obtain a natural tan and without producing a sunburn.

The pyridine derivatives employed in the composition of the present invention are known and can be prepared in accordance with procedures described in the literature, including the acetylation of an amino-pyridine, followed by oxidation of the resulting acetylamino pyridine and subsequent hydrolysis of the resulting acetamino pyridine N-oxide to provide amino pyridine N-oxide.

The pyridine derivatives can be prepared more particularly in accordance with the following process:

A—Preparation of acetylamino pyridine.

0.1 mole of amino pyridine is dissolved in 10 cc of acetic acid. To the resulting solution there is added with agitation 0.15 mole of acetic anhydride. The mixture is then heated at reflux for 3 hours at which time the acetic acid and acetic anhydride are distilled under reduced pressure. The resulting syrup crystallizes on cooling.

B—Preparation of acetylamino pyridine N-oxide.

0.1 mole of crude acetylamino pyridine is added, with agitation, to 20 cc of a 40% solution of peracetic acid in acetic acid. The mixture is heated for 4 hours at 70° C. and then evaporated to dryness under reduced pressure. Acetylamino pyridine N-oxide crystallizes on cooling.

C—Preparation of amino pyridine N-oxide.

A solution of 0.1 mole of acetylamino pyridine N-oxide in 50 cc of 5 N HCl is heated at reflux for two hours. The solvent is distilled under reduced pressure and the crystalline mass thus obtained is pasted in 50–100 cc of acetone. The resulting amino pyridine N-oxide hydrochloride is then filtered, washed with acetone and recrystallized.

The following non-limiting examples are given to illustrate the invention. Unless otherwise specified, all parts and percentages are by weight.

EXAMPLE 1—NONIONIC-BASED EMULSION

Nonionic emulsions are prepared and contain:
(a) 10–18% of an emulsifying agent comprising Sipol wax (mixture of stearyl alcohol and oleo-cetyl alcohol oxyethylenated with 25 moles of ethylene oxide), glycerol monostearate and cetyl alcohol;
(b) 10–20% of an oil comprising a silicone oil, sold under the mark RHODORSIL 47 V 300, which is a dimethylpolysiloxane having a viscosity of 300 cp at 25° C., a flash point of 320° C., a density at 20° C. of 0.95–0.97, and petrolatum oil-Codex;
(c) 1–20 percent of a humectant comprising glycerine;
(d) 0–1% perfume;

(e) 1–5% of the pyridine derivative of formula (I); and (f) water, sufficient for 100%.

The pH of this composition is between 5 and 6 and is stored in a bottle out of contact with light.

This composition is applied to the skin or on an inert support using conventional spreading means.

This procedure imparts to the skin a coloration resembling a natural tan after an exposure to light rays as defined above, for a period ranging from 5 to 30 minutes. In order to provide a more objective evaluation of the results, which are not influenced by the nature or the initial appearance of the human skin, or by the solar illumination which can be variable, most of the following tests have been carried out using an inert support.

A specific composition of this invention in the form of an oil-in-water emulsion is prepared by admixing the following components:

| | |
|---|---|
| Sipol wax (mixture of stearyl alcohol and oleo-cetyl alcohol oxythylenated with 25 moles of ethylene oxide) | 7 g |
| Glycerol monostearate | 2 g |
| Cetyl alcohol | 1.5 g |
| Silicone oil (sold under the mark RHODORSIL 47V300) | 1.5 g |
| Petrolatum oil - Codex | 15 g |
| Glycerine | 10 g |
| Perfume (sold under the mark CREMATEST 094990) | 0.5 g |
| 2-amino pyridine N-oxide hydrochloride | 3 g |
| Water, sufficient for | 100 g |

This composition which had been stored out of contact with light for several days was applied to the skin. After exposure of the thus treated skin to the bright midday sun, for a period of 10–20 minutes, a coloration similar to a natural tan developed on the skin.

The application of this same composition to an inert support comprising a glass plate also provided after an exposure of about 10–20 minutes to ultra violet rays a brown coloration resembling that of a natural tan.

Using essentially the same composition but replacing a portion of the petrolatum oil-CODEX with 1.5 g of benzylidene camphor, there resulted on the inert support, a deepening of the color identical to that previously obtained, at the end of 15–25 minutes.

By replacing the 2-amino pyridine N-oxide hydrochloride with another photo-dye responding to formula I, results set forth in Table I were achieved. These tests have been carried out as mentioned above on an inert support to provide a more objective reference. However, the color developed on the inert support is essentially the same natural tan coloration achieved when the same composition is applied to human skin.

Similar results are obtained by varying the amount of the different components of the composition within said ranges specified above.

The pH of these compositions varies with the photo-dye added. The pH is, for example, equal to 4 for the composition given in Table I and containing 2.5 wt.percent of 2-amino pyridine N-oxide hydrochloride.

EXAMPLE 2—IONIC-BASED EMULSION

Ionic-based emulsions are prepared and contain:

(a) 10–16% of an emulsifying agent comprising self-emulsifiable glycerine monostearate (sold under the mark ARLACEL 165), sorbitan monostearate polyoxyethylenated with 60 moles of ethylene oxide (sold under the mark TWEEN 60), stearic acid (triple pressure) and cetyl alcohol;

(b) 35–50% of an oil comprising petrolatum oil-CODEX;

(c) 0–1% triethanolamine;

(d) 0–1% perfume;

(e) 1–5% of the pyridine derivative of formula (I); and (f) water sufficient for 100%.

The pH of these compositions is adjusted to 7.

As in Example 1, the ionic-based emulsion is applied to the skin or onto the same inert support. As before, at the end of a period ranging from 10 minutes to 20 minutes, the appearance of a coloration essentially the same as that obtained using the same compound in Example 1 is achieved.

Using an emulsion having the following composition:

| | |
|---|---|
| Self-emulsifiable glycerine monostearate (sold under the mark ARLACEL 165) | 6 g |
| Sorbitan monostearate polyoxyethylenated with 60 moles of ethylene oxide (sold under the mark TWEEN 60) | 2 g |
| Stearic acid, pure, triple pressure | 2 g |
| Cetyl alcohol | 1.2 g |
| Petrolatum oil - CODEX | 38.5 g |
| Triethanolamine | 0.1 g |
| Perfume (sold under the mark No. 959/2) | 0.5 g |
| 2-amino-3-methyl pyridine N-oxide hydrochloride | 3 g |
| Water, sufficient for | 100 g | a brown coloration, on normal skin after a 20 minute exposure to the bright midday sun is achieved, this coloration being essentially the same as a natural tan.

The use of a solar filter and/or another pyridine derivative of Formula (I) in various other compositions provides those results set forth in Table II. The tests leading to these results have been carried out, as before, on an inert support.

Similar results are obtained by varying the amount and nature of the different components in these compositions.

EXAMPLE 3—LOTIONS

A composition of the present invention in lotion form is prepared and contains:

(a) 0.5–2% of lanolin ethoxylated with 25 moles of ethylene oxide;

(b) 0.5–5% of polyethylene glycol (M.W.=400);

(c) 1–10% of sorbitol (70%);

(d) 40–60% ethyl alcohol (96°);

(e) 0–1% of perfume;

(f) 1–5% of the pyridine derivative of formula (I); and (g) water, sufficient for 100%.

This lotion is applied to the skin, for example, by spraying and provides after exposure to the sun for a period between 10 and 20 minutes, a coloration essentially the same as a natural tan.

Using a lotion having the following composition:

| | |
|---|---|
| Lanolin, ethoxylated with 25 moles of ethylene oxide | 1 g |

-continued

| | |
|---|---|
| Polyethylene glycol (M.W. = 400) | 1 g |
| Sorbitol (70% in water) | 5 g |
| Ethyl alcohol, 96° titer | 50 g |
| Perfume (Robertet 13.999) | 0.5 g |
| 2-amino methyl pyridine N-oxide hydrochloride | 3 g |
| Water, sufficient for | 100 g | a coloration resembling a natural tan is achieved after an exposure of 20 minutes to a bright midday sun.

The inclusion of an ethoxylated derivative of p-aminobenzoic acid in an amount of 1.5% based on the ethyl alcohol, provides after an exposure of 30 minutes to the sun to a tan coloration essentially the same as that obtained above.

By replacing the photo-dye and/or filter by the components listed in Table III, the results shown therein are achieved. These tests, as before, have been made using an inert support.

Amerscreen P is the mark for a product comprising ethyl monohydroxy propylamino benzoate and ethyl dihydroxy propyl amino benzoate in a ratio of 1:3, which has a molecular weight of 281.

SC 9155 is the mark for a solar filter having fixed on a mole of p-amino benzoic acid about 25 moles of ethylene oxide; it has an OH index of 75.85 and a saponification index of 36.44.

TABLE I

| Photo-dye | | Nonionic Emulsion Filter | | Time of | |
|---|---|---|---|---|---|
| Nature | Amount wt % | Nature | Amount wt % | Exposure (min) | Coloration Achieved |
| 2-amino-pyridine N-oxide hydrochloride | 2.5 | | | 20 | light bronze brown |
| 2-amino-pyridine N-oxide hydrochloride | 5 | | | 15 | light bronze brown |
| 2-amino-pyridine N-oxide hydrochloride | 2.5 | amyl p-dimethyl amino benzoate | 3 | 30 | pale brown |
| 2-amino-pyridine N-oxide hydrochloride | 2.5 | ethyl hexyl p-methoxycinnamate | 1.5 | 30 | pale brown |
| 2-amino-pyridine N-oxide hydrochloride | 5 | benzylidene camphor | 2.5 | 30 | light bronze brown |
| 2-amino-3-methyl pyridine N-oxide hydrochloride | 5 | | | 20 | yellow ocher |
| 2-amino-4-methyl pyridine N-oxide hydrochloride | 2.5 | | | 20 | beige brown |
| 2-amino-4-methyl pyridine N-oxide hydrochloride | 5 | | | 15 | light bronze brown |
| 2-amino-4-methyl pyridine N-oxide hydrochloride | 2.5 | ethyl hexyl p-methoxy cinnamate | 1.5 | 30 | beige brown |
| 2-amino-4-methyl pyridine N-oxide hydrochloride | 2.5 | amyl p-dimethylamino benzoate | 3 | 35 | beige brown |
| 2-amino-4-methyl-pyridine N-oxide hydrochloride | 5 | benzylidene camphor | 2.5 | 30 | light bronze brown |
| 2-amino-5-methyl pyridine N-oxide hydrochloride | 5 | | | 20 | beige yellow |
| 2-amino-6-methyl pyridine N-oxide hydrochloride | 2.5 | | | 20 | beige brown |
| 2-amino-6-methyl pyridine N-oxide hydrochloride | 5 | | | 15 | beige brown |
| 2-amino-6-methyl pyridine N-oxide hydrochloride | 5 | benzylidene camphor | 2.5 | 30 | beige |
| 2-amino-6-methyl pyridine N-oxide hydrochloride | 2.5 | amyl p-dimethylamino benzoate | 3 | 30 | beige white |
| 2-amino-6-methyl pyridine N-oxide hydrochloride | 2.5 | ethyl hexyl p-methoxy cinnamate | 1.5 | 30 | yellow beige |
| 2-amino-4,6-dimethyl pyridine N-oxide hydrochloride | 5 | | | 20 | light bronze brown |
| 2-amino-5-chloro-pyridine N-oxide hydrochloride | 2.5 | | | 15 | chestnut beige |
| 2-amino-5-chloro-pyridine N-oxide hydrochloride | 5 | | | 10 | bronze brown |
| 2-amino-5-chloro-pyridine N-oxide hydrochloride | 5 | benzylidene camphor | 2.5 | 25 | bronze brown |
| 2-amino-5-chloro-pyridine N-oxide hydrochloride | 2.5 | ethyl hexyl p-methoxy cinnamate | 1.5 | 25 | chestnut beige |
| 2-amino-5-chloro-pyridine N-oxide hydrochloride | 2.5 | amyl p-dimethyl amino benzoate | 3 | 30 | light chestnut |
| 3-amino-pyridine N-oxide hydrochloride | 2.5 | | | 10 | chestnut brown |
| 3-amino-pyridine N-oxide hydrochloride | 5 | | | 10 | chestnut brown |
| 3-amino-pyridine N-oxide hydrochloride | 2.5 | amyl p-dimethyl amino benzoate | 3 | 25 | brown |
| 3-amino-pyridine N-oxide hydrochloride | 2.5 | ethyl hexyl p-methoxy cinnamate | 1.5 | 20 | brown |
| 3-amino-pyridine N-oxide hydrochloride | 4 | AMERSCREEN P | 4 | 15 | brown |
| 3-amino-pyridine N-oxide hydrochloride | 4 | AMERSCREEN P | 2 | 10 | brown |
| 3-amino-6-methyl pyridine | | | | | |

TABLE I-continued

| Photo-dye | | Nonionic Emulsion Filter | | Time of | |
|---|---|---|---|---|---|
| Nature | Amount wt % | Nature | Amount wt % | Exposure (min) | Coloration Achieved |
| N-oxide hydrochloride 3-amino-6-hydroxy pyridine N-oxide hydrochloride | 5 | | | 15 | yellow brown |
| 3-amino-6-hydroxy pyridine N-oxide hydrochloride | 2 | | | 10 | black chestnut |
| 3-amino-6-hydroxy pyridine N-oxide hydrochloride | 5 | | | 10 | black |
| 3-amino-pyridine N-oxide hydrochloride and 3-amino-6-hydroxy pyridine N-oxide hydrochloride | 1<br>1 | | | 10 | black chestnut |
| 3-amino-6-methyl pyridine N-oxide hydrochloride and 3-amino-6-hydroxy pyridine N-oxide hydrochloride | 1<br>1 | | | 10 | orange brown |
| 4-amino-pyridine N-oxide hydrochloride | 5 | | | 20 | beige |

TABLE II

| Photo-dye | | Ionic Emulsion Filter | | Time of | |
|---|---|---|---|---|---|
| Nature | Amount wt % | Nature | Amount wt % | Exposure (min) | Coloration Achieved |
| 2-amino-pyridine N-oxide hydrochloride | 2.5 | | | 20 | light bronze brown |
| 2-amino-pyridine N-oxide hydrochloride | 2.5 | amyl p-dimethyl amino benzoate | 3 | 30 | pale brown |
| 2-amino-pyridine N-oxide hydrochloride | 2.5 | ethyl hexyl p-methoxy cinnamate | 1.5 | 30 | pale brown |
| 2-amino-pyridine N-oxide hydrochloride | 5 | benzylidene camphor | 2.5 | 25 | light bronze brown |
| 2-amino-3-methyl pyridine N-oxide hydrochloride | 5 | | | 20 | yellow ocher |
| 2-amino-4-methyl pyridine N-oxide hydrochloride | 2.5 | | | 20 | light bronze brown |
| 2-amino-4-methyl pyridine N-oxide hydrochloride | 5 | | | 15 | light bronze brown |
| 2-amino-4-methyl pyridine N-oxide hydrochloride | 2.5 | amyl p-dimethyl amino benzoate | 3 | 35 | beige brown |
| 2-amino-4-methyl pyridine N-oxide hydrochloride | 2.5 | ethyl hexyl p-methoxy cinnamate | 1.5 | 30 | beige brown |
| 2-amino-4-methyl pyridine N-oxide hydrochloride | 5 | benzylidene camphor | 2.5 | 30 | beige brown |
| 2-amino-6-methyl pyridine N-oxide hydrochloride | 2.5 | | | 20 | beige brown |
| 2-amino-6-methyl pyridine N-oxide hydrochloride | 5 | | | 15 | beige brown |
| 2-amino-6-methyl pyridine N-oxide hydrochloride | 5 | benzylidene camphor | 2.5 | 30 | beige |
| 2-amino-6-methyl pyridine N-oxide hydrochloride | 2.5 | ethyl hexyl p-methoxy cinnamate | 1.5 | 30 | beige brown |
| 2-amino-6-methyl pyridine N-oxide hydrochloride | 2.5 | amyl p-dimethyl amino benzoate | 3 | 35 | beige |
| 2-amino-5-chloro-pyridine N-oxide hydrochloride | 2.5 | | | 15 | light bronze brown |
| 2-amino-5-chloro-pyridine N-oxide hydrochloride | 5 | | | 10 | light bronze brown |
| 2-amino-5-chloro-pyridine N-oxide hydrochloride | 2.5 | amyl p-dimethylamino benzoate | 3 | 30 | yellow brown |
| 2-amino-5-chloro pyridine N-oxide hydrochloride | 2.5 | 5-benzoyl-4-hydroxy-2-methoxy benzene sulfonic acid | 1.5 | 30 | beige brown |
| 2-amino-5-chloro pyridine N-oxide hydrochloride | 5 | benzylidene camphor | 2.5 | 30 | yellow brown |
| 3-amino-pyridine N-oxide hydrochloride | 2.5 | | | 10 | red brown |
| 3-amino-pyridine N-oxide hydrochloride | 5 | | | 10 | red brown |
| 3-amino-pyridine N-oxide hydrochloride | 5 | benzylidene camphor | 2.5 | 20 | red brown |

TABLE II-continued

| Photo-dye | | Ionic Emulsion Filter | | Time of Exposure (min) | Coloration Achieved |
|---|---|---|---|---|---|
| Nature | Amount wt % | Nature | Amount wt % | | |
| 3-amino-pyridine N-oxide hydrochloride | 2.5 | AMERSCREEN P | 2 | 20 | brown |
| 3-amino-pyridine N-oxide hydrochloride | 2.5 | ethyl hexyl p-methoxy cinnamate | 1.5 | 25 | brown |
| 3-amino-6-methyl pyridine N-oxide hydrochloride | 5 | | | 15 | yellow brown |
| 3-amino-6-methyl pyridine N-oxide hydrochloride | 5 | benzylidene camphor | 2.5 | 30 | yellow brown |

TABLE III

| Photo-dye | | Hydroalcoholic Lotion Filter | | Time of Exposure (min) | Coloration Achieved |
|---|---|---|---|---|---|
| Nature | Amount wt % | Nature | Amount wt % | | |
| 2-amino-pyridine N-oxide hydrochloride | 2.5 | | | 20 | golden yellow |
| 2-amino-pyridine N-oxide hydrochloride | 5 | | | 20 | yellow ocher |
| 2-amino-pyridine N-oxide hydrochloride | 2.5 | 5-benzoyl-4-hydroxy-2-methoxy benzene sulfonic acid | 3 | 40 | yellow beige |
| 2-amino-pyridine N-oxide hydrochloride | 5 | 2-hydroxy 4-methoxy benzophenone 5-sulfonic acid | 3 | 40 | yellow |
| 2-amino-3-methyl pyridine N-oxide hydrochloride | 5 | | | 20 | yellow ocher |
| 2-amino-4-methyl pyridine N-oxide hydrochloride | 5 | | | 20 | light bronze brown |
| 2-amino-4-methyl pyridine N-oxide hydrochloride | 5 | hydroxypropyleneted derivative of p-amino benzoic acid (SC 9155) | 1.5 | 35 | yellow beige |
| 2-amino-5-methyl pyridine N-oxide hydrochloride | 5 | | | 20 | yellow beige |
| 2-amino-6-methyl pyridine N-oxide hydrochloride | 5 | | | 20 | light bronze brown |
| 2-amino-6-methyl pyridine N-oxide hydrochloride | 5 | 5-benzoyl-4-hydroxy-2-methoxy benzene sulfonic acid | 1.5 | 40 | yellow beige |
| 2-amino-4,6-dimethyl pyridine N-oxide hydrochloride | 5 | | | 20 | yellow bronze brown |
| 2-amino-4,6 dimethyl pyridine N-oxide hydrochloride | 5 | diethanolamine salt of p-methoxy cinnamic acid | 1.5 | 40 | yellow ocher |
| 2-amino-5-chloro-pyridine N-oxide hydrochloride | 5 | | | 20 | bronze brown |
| 2-amino-5-chloro-pyridine N-oxide hydrochloride | 5 | hydroxypropylenated derivative of p-amino benzoic acid sold under the mark SC 9155 | 1.5 | 35 | yellow |
| 3-amino pyridine N-oxide hydrochloride | 2.5 | | | 15 | brown |
| 3-amino pyridine N-oxide hydrochloride | 5 | | | 10 | brown |
| 3-amino pyridine N-oxide hydrochloride | 2.5 | 5-benzoyl-4-hydroxy-2-methoxy benzene sulfonic acid | 3 | 35 | brown |
| 3-amino pyridine N-oxide hydrochloride | 5 | AMERSCREEN P | 1.5 | 25 | brown |
| 3-amino-6-methyl pyridine N-oxide hydrochloride | 5 | | | 15 | yellow brown |
| 3-amino-6-methyl pyridine N-oxide hydrochloride | 5 | AMERSCREEN P | 1.5 | 35 | yellow brown |
| 3-amino-6-hydroxy pyridine N-oxide hydrochloride | 2 | | | 10 | black brown |
| 3-amino-6-hydroxy pyridine N-oxide hydrochloride | 2 | 5-benzoyl-4-hydroxy-2-methoxy benzene sulfonic acid | 1.5 | 15 | black brown |
| 4-amino pyridine N-oxide | | | | | |

TABLE III-continued

| Photo-dye | | Hydroalcoholic Lotion | | Time of | |
| | | Filter | | | |
| Nature | Amount wt % | Nature | Amount wt % | Exposure (min) | Coloration Achieved |
| hydrochloride | 5 | | | 20 | beige |

What is claimed is:

1. A cosmetic composition for imparting to human skin after exposure to sunlight a coloration resembling a natural tan comprising a cosmetic vehicle, suitable for topical application to the skin, selected from the group consisting of (i) a hydroalcoholic solution, (ii) a glycerin-alcoholic solution and (iii) a glycerine hydroalcoholic solution of at least one compound selected from the group consisting of (a) a compound of the formula

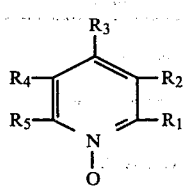

wherein
$R_1$ represents hydrogen or amino,
$R_2$ represents hydrogen, lower alkyl or amino,
$R_3$ represents hydrogen, lower alkyl or amino,
$R_4$ represents hydrogen, lower alkyl or chlorine,
$R_5$ represents hydrogen, lower alkyl or hydroxy, or when $R_1$ is amino, $R_5$ can also represent amino, with the proviso that $R_1$, $R_2$ and $R_3$ are not simultaneously amino, and at least one of $R_1$, $R_2$ and $R_3$ is amino, and (b) an acid addition salt of the compound in (a), said alcohol being ethanol or isopropanol and being present in said cosmetic vehicles (i), (ii) and (iii) in an amount between 10 and 90 weight percent thereof and said glycerine being present in said cosmetic vehicles (ii) and (iii) in an amount between 0.5 and 5 weight percent thereof, and said compound being present in an amount of 0.5-10 weight percent of said composition.

2. A cosmetic composition for imparting to human skin after exposure to sunlight a coloration resembling a natural tan comprising a cosmetic vehicle suitable for topical application to the skin comprising an oleoalcohol composition containing a vegetable oil, a lower alkyl ester and a lower alcohol having 1-4 carbon atoms, and at least one compound selected from the group consisting of (a) a compound of the formula

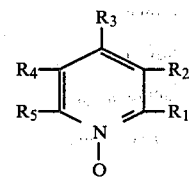

wherein
$R_1$ represents hydrogen or amino,
$R_2$ represents hydrogen, lower alkyl or amino,
$R_3$ represents hydrogen, lower alkyl or amino,
$R_4$ represents hydrogen, lower alkyl or chlorine,
$R_5$ represents hydrogen, lower alkyl or hydroxy, or when $R_1$ is amino, $R_5$ can also represent amino, with the proviso that $R_1$, $R_2$ and $R_3$ are not simultaneously amino, and at least one of $R_1$, $R_2$ and $R_3$ is amino, and (b) an acid addition salt of the compound in (a), said vegetable oil being present in an amount of 0.2 to 5 weight percent of the total weight of said cosmetic composition, said alkyl ester being present in an amount of 5 to 40 weight percent of the total weight of said cosmetic composition, said alcohol being present in an amount of 35-80 weight percent of the total weight of said cosmetic composition and said compound being present in an amount of 0.5 to 3 weight percent of said cosmetic composition.

3. The composition of claim 2 wherein said vegetable oil is colza oil, olive oil, peanut oil, coconut oil or palm oil.

4. The composition of claim 2 wherein said alkyl ester is isopropyl myristate or isopropyl palmitate.

5. The composition of claim 2 wherein said alcohol is ethanol.

6. A cosmetic composition for imparting to human skin after exposure to sunlight a coloration resembling a natural tan comprising a cosmetic vehicle suitable for topical application to the skin comprising an aqueous gel including a surfactant and a gel forming agent, and at least one compound selected from the group consisting of (a) a compound of the formula

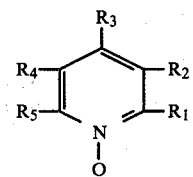

wherein
$R_1$ represents hydrogen or amino,
$R_2$ represents hydrogen, lower alkyl or amino,
$R_3$ represents hydrogen, lower alkyl or amino,
$R_4$ represents hydrogen, lower alkyl or chlorine,
$R_5$ represents hydrogen, lower alkyl or hydroxy, or when $R_1$ is amino, $R_5$ can also represent amino, with the proviso that $R_1$, $R_2$ and $R_3$ are not simultaneously amino, and at least one of $R_1$, $R_2$ and $R_3$ is amino, and (b) an acid addition salt of the compound in (a), said surfactant being present in an amount of 1-25 weight percent of the total weight of said cosmetic composition, said gel forming agent being present in an amount of 0.5-5 weight percent of the total weight of said cosmetic composition and said compound being present in an amount of 0.5-10 weight percent of said cosmetic composition.

7. The composition of claim 6 wherein said surfactant is a fatty alcohol having 12-18 carbon atoms oxyethylenated with 4-15 moles of ethylene oxide, nonylphenol oxyethylenated with 6-12 moles of ethylene oxide or a carboxylic derivative of imidazole.

8. The composition of claim 6 wherein said gel forming agent is cellulose ether, carboxy methyl cellulose or crosslinked polyacrylic acid.

9. A cosmetic composition for imparting to human skin after exposure to sunlight a coloration resembling a natural tan comprising a cosmetic vehicle, suitable for topical application to the skin, selected from the group consisting of
   (1) a hydroalcoholic solution containing 10-90 weight percent alcohol,
   (2) an ethanolic glycerine lotion,
   (3) an oleoethanolic composition containing a vegetable oil, a lower alkyl ester and an alcohol containing 1-4 carbon atoms,
   (4) an aqueous gel including a surfactant and a gel forming agent, and
   (5) an oil-in-water emulsion including a surfactant, an oil, a thickening agent and a humectant,
0.5-10 weight percent of said composition of at least one compound selected from the group consisting of
   (a) a compound of the formula:

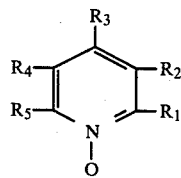

wherein
   $R_1$ represents hydrogen or amino,
   $R_2$ represents hydrogen, lower alkyl or amino,
   $R_3$ represents hydrogen, lower alkyl or amino,
   $R_4$ represents hydrogen, lower alkyl or chlorine,
   $R_5$ represents hydrogen, lower alkyl or hydroxyl, or when $R_1$ is amino, $R_5$ can also represent amino, with the proviso that $R_1$, $R_2$ and $R_3$ are not simultaneously amino, and at least one of $R_1$, $R_2$ and $R_3$ is amino, and
   (b) an acid addition salt of the compound in (a), and
   0.5-5 percent by weight of a solar filter.

10. The composition of claim 9 wherein said solar filter is selected from the group consisting of benzylidene camphor, ethyl hexyl p-methoxy cinnamate, amyl p-dimethylamino benzoate, 5-benzoyl-4-hydroxy-2-methoxy benzene sulfonic acid, hydroxy propylenated derivative of ethyl p-amino benzoate and the diethanolamine salt of p-methoxy cinnamic acid.

11. A cosmetic composition for imparting to human skin after exposure to sunlight a coloration resembling a natural ten comprising a cosmetic vehicle, suitable for topical application to the skin, which is an oleoethanolic composition containing a vegetable oil, a lower alkyl ester and an alcohol containing 1-4 carbon atoms, said vegetable oil being present in an amount of 5-40 weight percent, the alcohol being present in an amount of 35-80 weight percent and the alkyl ester being present in an amount of 5-40 weight percent, and 0.5-10 weight percent of said composition of at least one compound selected from the group consisting of
   (a) a compound of the formula

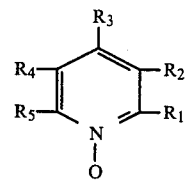

wherein
   $R_1$ represents hydrogen or amino,
   $R_2$ represents hydrogen, lower alkyl or amino,
   $R_3$ represents hydrogen, lower alkyl or amino,
   $R_4$ represents hydrogen, lower alkyl or chlorine,
   $R_5$ represents hydrogen, lower alkyl or hydroxy, or where $R_1$ is amino, $R_5$ can also represent amino, with the proviso that $R_1$, $R_2$ and $R_3$ are not simultaneously amino, and at least one of $R_1$, $R_2$ and $R_3$ is amino, and
   (b) an acid addition salt of the compound in (a).

12. A cosmetic composition packaged under pressure in an aerosol container for imparting to human skin after exposure to sunlight a coloration resembling a natural tan comprising a cosmetic vehicle, suitable for topical application to the skin, selected from the group consisting of
   (1) a hydroalcoholic solution containing 10-90 weight percent alcohol,
   (2) an ethanolic glycerine lotion,
   (3) an oleoethanolic composition containing a vegetable oil, a lower alkyl ester and an alcohol containing 1-4 carbon atoms,
   (4) an aqueous gel including a surfactant and a gel forming agent, and
   (5) an oil-in-water emulsion including a surfactant, an oil, a thickening agent and a humectant, and
0.5-10 weight percent of said composition of at least one compound selected from the group consisting of
   (a) a compound of the formula:

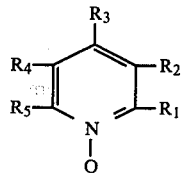

wherein
   $R_1$ represents hydrogen or amino,
   $R_2$ represents hydrogen, lower alkyl or amino,
   $R_3$ represents hydrogen, lower alkyl or amino,
   $R_4$ represents hydrogen, lower alkyl or chlorine,
   $R_5$ represents hydrogen, lower alkyl or hydroxyl, or when $R_1$ is amino, $R_5$ can also represent amino, with the proviso that $R_1$, $R_2$ and $R_3$ are not simultaneously amino, and at least one of $R_1$, $R_2$ and $R_3$ is amino, and
   (b) an acid addition salt of the compound in (a).

13. A cosmetic composition for imparting to human skin after exposure to sunlight a coloration resembling a natural tan comprising a cosmetic vehicle suitable for topical application to the skin comprising an oil-in-water emulsion, said emulsion containing 2 to 20 weight percent surfactant, 10-50 weight percent fatty phase, 0-6 weight percent thickening agent and 0-15 weight percent humectant, and at least one compound selected from the group consisting of (a) a compound of the formula

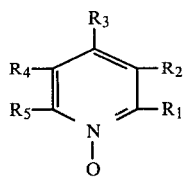

wherein
R₁ represents hydrogen or amino,
R₂ represents hydrogen, lower alkyl or amino,
R₃ represents hydrogen, lower alkyl or amino,
R₄ represents hydrogen, lower alkyl or chlorine,
R₅ represents hydrogen, lower alkyl or hydroxy, or when R₁ is amino, R₅ can also represent amino, with the proviso that R₁, R₂ and R₃ are not simultaneously amino, and at least one of R₁, R₂ and R₃ is amino, and (b) an acid addition salt of the compound in (a), said compound being present in an amount of 0.5–10 weight percent of said cosmetic composition, and said surfactant is a fatty alcohol having 12–18 carbon atoms oxyethylenated with 10–15 moles of ethylene oxide, isopropyl palmitate, isopropyl myristate, glycerol monostearate, polyoxyethylenated sorbitan monostearate, partially sulfated or partially oxyethylenated cetyl-stearyl alcohol, or a mixture thereof.

14. The composition of claim 13 wherein said thickening agent is starch, crosslinked polyacrylic acid or diethylene glycol stearate.

15. The composition of claim 13 wherein said humectant is glycerine.

16. A cosmetic composition for imparting to human skin after exposure to sunlight a coloration resembling a natural tan comprising a cosmetic vehicle, suitable for topical application to the skin, wherein said cosmetic vehicle is an aqueous gel including a surfactant and a gel forming agent, and which also includes a silicone oil in an amount up to about 2 weight percent, and
0.5–10 weight percent of said composition of at least one compound selected from the group consisting of
(a) a compound of the formula:

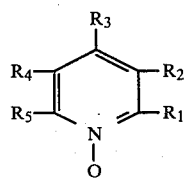

wherein
R1 represents hydrogen or amino,
R2 represents hydrogen, lower alkyl or amino,
R3 represents hydrogen, lower alkyl or amino,
R4 represents hydrogen, lower alkyl or chlorine,
R5 represents hydrogen, lower alkyl or hydroxyl, or when R₁ is amino, R₅ can also represent amino, with the proviso that R₁, R₂ and R₃ are not simultaneously amino, and at least one of R₁, R₂ and R₃ is amino, and (b) an acid addition salt of the compound in (a).

17. A cosmetic composition for imparting to human skin after exposure to sunlight a coloration resembling a natural tan comprising a cosmetic vehicle, suitable for topical application to the skin, wherein said cosmetic vehicle is an aqueous gel including a surfactant and a gel forming agent and wherein said surfactant is present in an amount of 1–25 weight percent and said gel forming agent is present in an amount of 0.5–4 weight percent, and
0.5–10 weight percent of said composition of at least one compound selected from the group consisting of
(a) a compound formula:

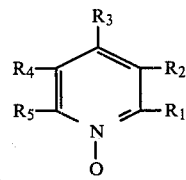

wherein
R₁ represents hydrogen or amino,
R₂ represents hydrogen, lower alkyl or amino,
R₃ represents hydrogen, lower alkyl or amino,
R₄ represents hydrogen, lower alkyl or chlorine,
R₅ represents hydrogen, lower alkyl or hydroxyl, or when R₁ is amino, R₅ can also represent amino, with the proviso that R1, R₂ and R₃ are not simultaneously amino, and at least one of R1, R₂ and R₃ is amino, and (b) an acid addition salt of the compound in (a).

18. A process for coloring human skin comprising applying to the skin a composition comprising
a cosmetic vehicle, suitable for topical applications to the skin, selected from the group consisting of
(1) a hydroalcoholic solution containing 10–90 weight percent alcohol,
(2) an ethanolic glycerine lotion,
(3) an oleoethanolic composition containing a vegetable oil, a lower alkyl ester and an alcohol containing 1–4 carbon atoms,
(4) an aqueous gel including a surfactant and a gel forming agent, and
(5) an oil-in-water emulsion including a surfactant, an oil, a thickening agent and a humectant, and
0.5–10 weight percent of said composition of at least one compound selected from the group consisting of
(a) a compound of the formula:

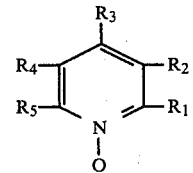

wherein
R₁ represents hydrogen or amino,
R₂ represents hydrogen, lower alkyl or amino,
R₃ represents hydrogen, lower alkyl or amino,
R₄ represents hydrogen, lower alkyl or chlorine,
R₅ represents hydrogen, lower alkyl or hydroxyl, or when R₁ is amino, R₅ can also represent amino, with the proviso that R₁, R₂ and R₃ are not simultaneously amino, and at least one of R₁, R₂ and R₃ is amino, and (b) an acid addition salt of the compound in (a), in an amount effective to color said skin after exposure to ultraviolet rays and exposing the skin to ultraviolet rays for a time effective to develop a color resembling a natural tan on the skin.

19. The process of claim 18 wherein said cosmetic vehicle is (3) and wherein said vegetable oil is present in an amount of 5-40 weight percent, the alcohol is present in an amount of 35-80 weight percent and the alkyl ester is present in an amount of 5-40 weight percent.

20. The process of claim 18, wherein said cosmetic vehicle is (4) and wherein said surfactant is present in an amount of 1-25 weight percent and said gel forming agent is present in an amount of 0.5-4 weight percent.

21. The process of claim 18, wherein said cosmetic vehicle is (4) and which also includes a silicone oil in an amount up to about 2 weight percent.

22. The process of claim 18, wherein said cosmetic vehicle is (5) and wherein said surfactant is present in an amount of 2-20 weight percent, said oil is present in an amount of 10-50 weight percent, said thickening agent is present in an amount of 0-6 weight percent and said humectant is present in an amount of 0-15 weight percent.

23. A process for imparting to human skin a coloration resembling a natural tan comprising applying to said skin a composition comprising a cosmetic vehicle, suitable for topical application to the skin, selected from the group consisting of (i) a hydroalcoholic solution, (ii) a glycerinalcoholic solution and (iii) a glycerine hydroalcoholic solution of at least one compound selected from the group consisting of
(a) a compound of the formula

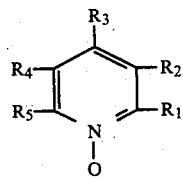

wherein
$R_1$ represents hydrogen or amino,
$R_2$ represents hydrogen, lower alkyl or amino,
$R_3$ represents hydrogen, lower alkyl or amino,
$R_4$ represents hydrogen, lower alkyl or chlorine,
$R_5$ represents hydrogen, lower alkyl or hydroxy, or when $R_1$ is amino, $R_5$ can also represent amino, with the proviso that $R_1$, $R_2$ and $R_3$ are not simultaneously amino, and at least one of $R_1$, $R_2$ and $R_3$ is amino, and
(b) an acid addition salt of the compound in (a), said alcohol being ethanol or isopropanol and being present in said cosmetic vehicles (i), (ii), and (iii) in an amount between 10 and 90 weight percent thereof and said glycerine being present in said cosmetic vehicles (ii) and (iii) in an amount between 0.5 and 5 weight percent thereof, and said compound being present in an amount of 0.5-10 weight percent of said composition;
in an amount effective to color said skin after exposure to ultraviolet rays and exposing the skin to ultraviolet rays for a time effective to develop a color resembling a natural tan on the skin.

24. A process for imparting to human skin after exposure to sunlight a coloration resembling a natural tan comprising applying to said skin a composition comprising a cosmetic vehicle suitable for topical application to the skin comprising an oleo-alcohol composition containing a vegetable oil, a lower alkyl ester and a lower alcohol having 1-4 carbon atoms, and at least one compound selected from the group consisting of
(a) a compound of the formula

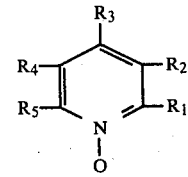

wherein
$R_1$ represents hydrogen or amino,
$R_2$ represents hydrogen, lower alkyl or amino,
$R_3$ represents hydrogen, lower alkyl or amino,
$R_4$ represents hydrogen, lower alkyl or chlorine,
$R_5$ represents hydrogen, lower alkyl or hydroxy, or when $R_1$ is amino, $R_5$ can also represent amino, with the proviso that $R_1$, $R_2$ and $R_3$ are not simultaneously amino, and at least one of $R_1$, $R_2$ and $R_3$ is amino, and
(b) an acid addition salt of the compound in (a), said vegetable oil being present in an amount of 0.2 to 5 weight percent of the total weight of said cosmetic composition, said alkyl ester being present in an amount of 5 to 40 weight percent of the total weight of said cosmetic composition, said alcohol being present in an amount of 35-80 weight percent of the total weight of said cosmetic composition and said compound being present in an amount of 0.5 to 3 weight percent of said cosmetic composition;
in an amount effective to color said skin after exposure to ultraviolet rays and exposing the skin to ultraviolet rays for a time sufficient to develop a color resembling a natural tan on the skin.

25. The process of claim 24 wherein said vegetable oil is colza oil, olive oil, peanut oil, coconut oil or palm oil.

26. The process of claim 24 wherein said alkyl ester is isopropyl myristate or isopropyl palmitate.

27. The process of claim 24 wherein said alcohol is ethanol.

28. A process for imparting to human skin after exposure to sunlight a coloration resembling a natural tan comprising applying to the skin a composition comprising a cosmetic vehicle suitable for topical application to the skin comprising an aqueous gel including a surfactant and a gel forming agent, and at least one compound selected from the group consisting of
(a) a compound of the formula

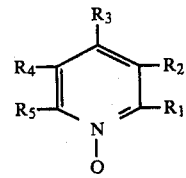

wherein
$R_1$ represents hydrogen or amino,
$R_2$ represents hydrogen, lower alkyl or amino,
$R_3$ represents hydrogen, lower alkyl or amino,
$R_4$ represents hydrogen, lower alkyl or chlorine, $R_5$ represents hydrogen, lower alkyl or hydroxy, or when $R_1$ is amino, $R_5$ can also represent amino, with the proviso that $R_1$, $R_2$ and $R_3$ are not simultaneously amino, and at least one of $R_1$, $R_2$ and $R_3$ is amino, and (b) an acid addition salt of the compound in (a), said surfactant being present in an amount of 1-25 weight percent of the total weight of said cosmetic composition, said gel forming agent being present in an amount of 0.5-5 weight percent of the total weight of said cosmetic composition and said compound being present in an amount of 0.5-10 weight percent of said cosmetic composition;

in an amount effective to color said skin after exposure to ultraviolet rays and exposing said skin to ultraviolet rays for a time effective to develop a color resembling a natural tan on the skin.

29. The process of claim 28 wherein said surfactant is a fatty alcohol having 12-18 carbon atoms oxyethylenated with 4-15 moles of ethylene oxide, nonylphenol oxyethylenated with 6-12 moles of ethylene oxide or a carboxylic derivative of imidazole.

30. The process of claim 28 wherein said gel forming agent is cellulose ether, carboxy methyl cellulose or crosslinked polyacrylic acid.

31. A process for imparting to human skin after exposure to sunlight a coloration resembling a natural tan comprising applying to the skin a composition comprising a cosmetic vehicle suitable for topical application to the skin comprising an oil-in-water emulsion, said emulsion containing 2 to 20 weight percent surfactant, 10-50 weight percent fatty phase, 0-6 weight percent thickening agent and 0-15 weight percent humectant, and at least one compound selected from the group consisting of (a) a compound of the formula

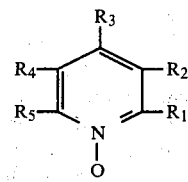

wherein
$R_1$ represents hydrogen or amino,
$R_2$ represents hydrogen, lower alkyl or amino,
$R_3$ represents hydrogen, lower alkyl or amino,
$R_4$ represents hydrogen, lower alkyl or chlorine,
$R_5$ represents hydrogen, lower alkyl or hydroxy, or when $R_1$ is amino, $R_5$ can also represent amino, with the proviso that $R_1$, $R_2$ and $R_3$ are not simultaneously amino, and at least one of $R_1$, $R_2$ and $R_3$ is amino, and (b) an acid addition salt of the compound in (a),
said compound being present in an amount of 0.5-10 weight percent of said cosmetic composition;
in an amount effective to color said skin after exposure to ultraviolet rays and exposing said skin to ultraviolet rays for a time effective to develop a color resembling a natural tan on the skin.

32. The process of claim 31 wherein said surfactant is a fatty alcohol having 12-18 carbon atoms oxyethylenated with 10-15 moles of ethylene oxide, isopropyl palmitate, isopropyl myristate, glycerol monostearate, polyoxyethylenated sorbitan monostearate, partially sulfated or partially oxyethylenated cetyl-stearyl alcohol, or a mixture thereof.

33. The process of claim 31 wherein said fatty phase is light petrolatum oil, perhydrosqualene, sweet almond oil, ricin oil, colza oil, olive oil, peanut oil, coconut oil, palm oil, a fatty alcohol having 7 carbon atoms or a saturated fatty acid having 18 carbon atoms.

34. The process of claim 33 wherein said thickening agent is starch, crosslinked polyacrylic acid or diethylene glycol stearate.

35. The process of claim 33 wherein said humectant is glycerine.

* * * * *